United States Patent
Das et al.

(10) Patent No.: US 10,030,002 B2
(45) Date of Patent: Jul. 24, 2018

(54) COUMARIN DERIVATIVE FOR DETECTION OF CYSTEINE AND PROCESS FOR THE SYNTHESIS THEREOF

(71) Applicant: COUNCIL OF SCIENTIFIC & INDUSTRIAL RESEARCH, New Delhi (IN)

(72) Inventors: Amitava Das, Pune (IN); Anila Ashoka Hoskere, Pune (IN); Upendar Reddy Gandra, Pune (IN); Firoj Ali, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/566,781

(22) PCT Filed: Apr. 13, 2016

(86) PCT No.: PCT/IN2016/050110
§ 371 (c)(1),
(2) Date: Oct. 16, 2017

(87) PCT Pub. No.: WO2016/166773
PCT Pub. Date: Oct. 20, 2016

(65) Prior Publication Data
US 2018/0093963 A1    Apr. 5, 2018

(30) Foreign Application Priority Data

Apr. 16, 2015  (IN) .......................... 1061/DEL/2015

(51) Int. Cl.
*C07D 311/16*   (2006.01)
*G01N 33/68*   (2006.01)

(52) U.S. Cl.
CPC ....... *C07D 311/16* (2013.01); *G01N 33/6815* (2013.01)

(58) Field of Classification Search
CPC .......................... C07D 311/16; G01N 33/6815
See application file for complete search history.

(56) References Cited

PUBLICATIONS

Yuan-Qiang Sun et al: "Nitroolefin-based coumarin as a colorimetric and fluorescent dual probe for biothiols", Chemical Communications—Chemcon., vol. 47, No. 39, 2011, p. 11029, XP055289272, ISSN: 1359-7345, DOI:10.1039/c1cc14299b.
Hongqi Li et al: "Coumarin-Derived Fluorescent Chemosensors" In: "Advances in Chemical Sensors", 2012, InTech, XP055148839, ISBN: 978-9-53-307792-5 pp. 121-150, DOI 10.5772/33157, p. 133; figure 12.
Anila H. A. et al: "A reagent for specific recognition of cysteine in aqueous buffer and in natural milk: imaging studies, enzymatic reaction and analysis of whey protein", Chemical Communications—Chemcom., vol. 51, No. 85, Aug. 26, 2015 (Aug. 26, 2015), pp. 15592-15595, XP055288880, ISSN: 1359-7345, DOI: 10.1039/C5CC04876A abstract; compound L.

*Primary Examiner* — Timothy R Rozof
(74) *Attorney, Agent, or Firm* — Eversheds Sutherland (US) LLP

(57) ABSTRACT

The present invention relates to a coumarin derivative of Formula (L) for detection of cysteine and process for preparation thereof. The present invention further relates to a process of detection of cysteine residues present in protein as well as the cysteine released by the enzymatic action of aminoacylase 1 by using coumarin derivative of Formula (L).

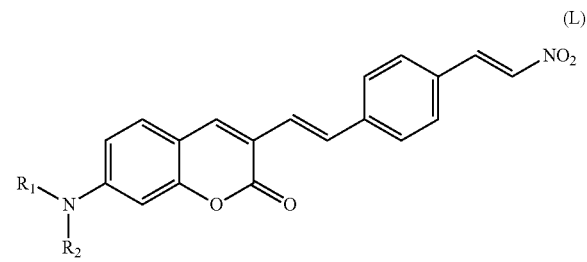

10 Claims, 9 Drawing Sheets

COUMARIN DERIVATIVE FOR DETECTION OF CYSTEINE AND PROCESS FOR THE SYNTHESIS THEREOF

FIELD OF THE INVENTION

The present invention relates to a coumarin derivative of Formula (L) for detection of cysteine and process for preparation thereof. The present invention further relates to a process of detection of cysteine by using coumarin derivative of Formula L.

BACKGROUND AND PRIOR ART

Biological thiols such as Cysteine (Cys), Homocysteine (Hcy) and Glutathione (GSH) play crucial roles in maintaining cellular antioxidant defence system. Among them cysteine plays many important roles in living systems. Cysteine is one of the three main precursors required for GSH synthesis. The deficiency of this compound causes many diseases such as slowed growth in children, depigmentation of hair, edema, liver damage, skin lesions, and weakness. An elevated level of Hcy is a risk factor for cardio-vascular disease, dementia and Alzheimer's disease. Abnormal levels of GSH is connected to many diseases such as HIV, cell death and aging. Thus, detection and discrimination of these thiol containing molecules are of great importance. Because of the similar structure and reactivity, distinction among biothiols is a challenging task. The respective concentration level of Cys in human plasma is typically 240-360 µM. Estimation of these amino thiols in human blood plasma is essential for understanding the role of these in the pathogenesis of vascular diseases.

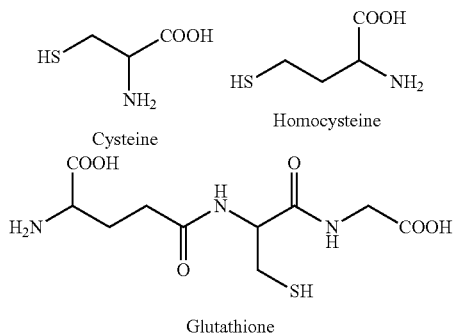

The past two decade has seen significant effort being devoted to the development of optical probes for the selective recognition of thiol containing amino acids. There are many strategies for sensing biothiols, based on Micheal addition, cyclization with aldehydes, disulfide cleavage and others.

Chinese Pat. No. 103570701 discloses a coumarin derivative and preparation method and application, the coumarin derivatives, the Formula $C_{13}H_6N_2O_4$. Preparation of the present invention, 2,2-dicyano-3-(7-hydroxy-4-coumarinyl) oxirane as a living body to selectively detect cysteine fluorescent probe, can also be used for fluorescence cysteine labeled cells within, for the diagnosis of related diseases in clinical medicine to help.

Chinese Pat. No. 103788076 discloses a method for quantitative detection of cysteine, is based on N-[4-methyl-coumarin-7-yl] maleimide in HEPES pH 7.4 solution quantitatively detect cysteine acid content. The detection method for cysteine showed high sensitivity and selectivity, the detection process is simple, sensitive, rapid, accurate test results.

Article titled "7-Diethylamino-3-{(E)-4-[(E)-2-(pyridin-4-yl)ethenyl]styryl}-2H-chromen-2-one" by Li-Ping Zhou et al. published in *Acta Crystallographica Section E Structure Reports Online*, 2014, 70(2), o176 reports coumarin derivative, $C_{28}H_{26}N_2O_2$, the coumarin unit is approximately planar, with a maximum deviation of 0.048 (3) Å. The central benzene ring is oriented at dihedral angles of 30.15 (14) and 10.51 (11°), respectively, to the pyridine ring and coumarin ring system. In the crystal, weak C—H . . . O and C—H . . . N hydrogen bonds and weak C—H . . . π interactions link the molecules into a three-dimensional supramolecular architecture.

Article titled "Thiol-chromene click chemistry: a coumarin-based derivative and its use as regenerable thiol probe and in bioimaging applications" by Yang Y et al. published in *Biosensors and Bioelectronics* 2013; 47:pp 300-6 reports the synthesis and characterization of a coumarin-chromene (8, 9-dihydro-2H-cyclopenta[b]pyrano[2,3-f]chromene-2,10 (7aH)-dione) (1) derivative and its use for thiol chemosensing in water was reported. Experimental details showed 1 acts as a probe for the detection of thiols including cysteine (Cys), homocysteine (Hcy) and glutathione (GSH), whereas amino acids which do not contain thiols induced no changes in UV-vis spectra and fluorescence emission properties of 1. A possible detection mechanism is a nucleophilic attack of thiols to the α,β-unsaturated ketone in 1 that resulted in a fluorescent coumarin derivative. Further studies showed that 1-thiol derivatives can be applied to the design of regenerative chemodosimeters for Cu(2+), Hg(2+) and Cd(2+) in water based on M(n+)-promoted desulfurization and recovery of 1. Furthermore, the optical properties of the probe and its Cys-addition product were theoretically studied. The ability of probe 1 to detect thiols in living cells (HepG2 cells) via an enhancement of the fluorescence was proved. Moreover, the applicability of 1 for the direct determination of biorelevant thiols in a complex matrix such as human plasma was also demonstrated.

Article titled "Nitroolefin-based coumarin as a colorimetric and fluorescent dual probe for biothiols" by Sun Y Q et al. published in *Chemical Communications*, 2011; 47(39) pp 11029-31 reports a coumarin-based thiol probe featuring the 1,4-addition reaction of thiols to nitroolefin was reported. The molecular probe exhibited higher selectivity toward biothiols (Cys, Hcy and GSH) than other amino acids.

Article titled "Coumarin-Derived Fluorescent Chemosensors." by Raman G et al. published in *Phytochem Analysis*, 2005; 16(3):155-60 reports Coumarin-derived fluorescent chemosensors for thiols. Study on fluorescent and colorimetric probes for detection of thiols has received much attention and many coumarin-derived fluorescent chemosensors for detection of thiols have been reported.

Article titled "Colorimetric detection of thiols using a chromene molecule" by Fang-Jun Huo et al. published in *Organic Letters*, 2009, 11(21), pp 4918-4921 reports a new thiol-containing colorimetric probe has been developed by using a chromene derivative, 7-nitro-2,3-dihydro-1H-cyclopenta[b]chromen-1-one. The molecule exhibited high selectivity and sensitivity for detecting thiol species as cysteine, homocysteine, and glutathione in aqueous solution through a rapid visual color change from colorless to yellow. The pH range (5.0-10.0) for determination of cysteine was also studied and the result showed that the system had the above-mentioned UV/visible light absorption with no significant difference within the pH range 7.0-10.0. Therefore selected the physiological condition of a HEPES 10 mM, pH 7.0 buffer aqueous solution. Systems with pH<7.0 will not exhibit a notable change in either color or UV/visible spectrum.

Article titled "The development of a fluorescence turn-on sensor for cysteine, glutathione and other biothiols. A kinetic study" by Olimpo Garcia-Beltran et al. published in *Tetrahedron Letters*, 2011, 52, pp 6606-6609 reports two fluorescence probes for the detection of cysteine (Cys), glutathione (GSH) and other biothiols, such as homocysteine (Hcy) and cysteinyl-glycine (Cys-Gly), were developed. These molecular probes are coumarin-based derivatives containing a chalcone-like moiety that reacts with biothiols through a Michael addition reaction, leading to strong fluorescence enhancements. The reactivity of the tested biothiols toward both probes (ChC1 and ChC2) follows the order Cys>GSH>Hcy>Cys-Gly, ChC1 being less reactive than ChC2. Possible interference with other amino acids was assessed.

ChC1 and ChC2 display a highly selective fluorescence enhancement with thiols, allowing these probes to be used for fluorimetric thiol determination in SH-SY5Y cells.

Article titled "Synthesis of coumarin derivatives as fluorescent probes for membrane and cell dynamics studies" by Olimpo Garcia-Beltran et al. published in *European Journal of Medicinal Chemistry*, 2014, 76, pp 79-86 reports three coumarin-derived fluorescent probes, 3-acetyl-7-[(6-bromohexyl)oxy]-2H-chromen-2-one (FM1), 7-[(6-bromohexyl)oxy]-4-methyl-2H-chromen-2-one (FM2) and ethyl 2-{7-[(6-bromohexyl)oxy]-2-oxo-2H-chromen-4-yl}acetate (FM3), are described, with their photophysical constants. All absorption and emission spectra were measured in a mixture of ACN:aqueous 20 mM HEPES buffer, pH 7.4, 1.1.

Article titled "New chemodosimetric reagents as ratiometric probes for cysteine and homocysteine and possible detection in living cells and in blood plasma" by Priyadip Das et al. published in *Chemistry*, 2012; 18(48), pp 15382-93 reports rationally designed and synthesized two new reagents (L1 and L2), each bearing a pendant aldehyde functionality. This aldehyde group can take part in cyclization reactions with b-org-amino thiols to yield the corresponding thiazolidine and thiazinane derivatives, respectively. The recognition of Cys/Hcy by L1 and L2 was investigated by monitoring the changes in the electronic spectra of these receptors upon the formation of their respective thiazolidine moieties. Thus, L1 and L2 were each treated with varying concentrations of Cys and Hcy in appropriate DMSO/aqueous HEPES buffer (pH 7.4) media. Upon addition of increasing amounts of Cys or Hcy to a solution of L1 in DMSO/aqueous HEPES buffer (50 mm, 3:2 (v/v), pH 7.4), the absorption band at around 397 nm was found to decrease gradually with a concomitant increase at around 460 nm. experiments were carried out to prove the above sensing mechanism. Firstly, the product mixture of the reaction of cysteamine (cysteamine was selected instead of Cys because of its good solubility in organic solvents) with 4 in CH$_3$OH was separated and 1,4-thiazepan-5-one (6) and the parent SNF were obtained, respectively. The structure of 6 was identified by $^1$H NMR, $^{13}$C NMR and HRMS. The formation of SNF was confirmed by a major peak at m/z 395.0929, corresponding to [SNF—H]$^-$(calc. 395.0919 for C$_{25}$H$_{15}$O$_5$) was shown in the HRMS data. Secondly, cysteamine and 3-mercaptopropanoic acid (MPA) were introduced to the solution of 4, respectively, and it was observed that the former gives a prominent increase in fluorescence emission but the latter produces weak fluorescence increase at the same conditions. Lastly, N-acetyl-1-cysteine (NAC) was added to a solution of 4 and almost no fluorescence increase was observed under the same conditions. The above experiments serve as strong evidence that both sulfhydril and amino groups (the NAC amine is blocked) of Cys are responsible for the signal.

Article titled "A seminaphthofluorescein-based fluorescent chemodosimeter for the highly selective detection of cysteine" by Xiaofeng Yang et al. published in *Organic and Molecular Chemistry*, 2012, 10(14), pp 2739-2741 reports a fluorescent chemodosimeter for cysteine detection was developed based on a tandem conjugate addition and intramolecular cyclization reaction. The method exhibited an excellent selectivity for cysteine over other biothiols such as homocysteine and glutathione. Color changes of the solution of 4 (10 µM) in the presence of different biothiols (2 equiv.) in 1.0 mM CTAB media buffered at pH 7.4 (Hepes buffer, 20 mM) after 25 min.

Article titled "Dicyclohexylcarbodiimide (DCC)" by Miroslav Kvasnica published in *Synlett*, 2007(14), pp 2306-2307 reports synthesis of amides, lactams and peptides by using DCC and DMAP. Heterocyclization reactions: DCC is widely used as a reagent (or reactant) in the synthesis of heterocycles. Jeon and co-workers published the solid-phase synthesis of 2-amino-2-thiazolines using the DCC-mediated cyclization of N-(2-hydroxyethyl) thioureas.

Article titled "A cysteine-selective fluorescent probe for the cellular detection of cysteine" by Jung H S et al. published in *Biomaterials*, 2012, 33(3), pp 945-953 reports a series of coumarin fluorophores, each bearing a double bond conjugated quinoline unit that can undergo a Michael-type reaction with thiol-containing compounds, is reported. These systems, designed to provide so-called turn-on changes in fluorescence response when exposed to thiols, act as fluorescent chemical sensors for cysteine (Cys), homocysteine (Hcy), and glutathione (GSH).

Article titled "Synthesis and vasorelaxant and platelet antiaggregatory activities of a new series of 6-Halo-3-phenylcoumarins" by Elias Quezada et al. published in *Molecules* 2010, 15, pp 270-279 reports 3-phenylcoumarins were prepared from the conveniently substituted phenylacetic acids, the appropriate salicylaldehyde and dicyclohexylcarbodiimide (DCC) by a Perkin reaction in dimethylsulfoxide (DMSO).

Article titled "The synthesis, characterization and properties of coumarin glycosides and coumarin-strapped calixpyrrole derivatives" by LiYang published in *Master's thesis* in 2011 reports designed and synthesized coumarin-strapped calix[4]pyrrole derivatives. With 2-Hydroxy-1-naphthaldehyde, 4-(Diethylamino) salicylaldehyde, salicylaldehyde and diethyl malonate as raw materials, pyridine and acetic acid as catalysts, coumarin esters were synthesized, and through hydrolysis reaction, coumarin acid compounds were got. Using DCC/DMAP method and carbonyl chlorides method, coumarin-Strapped calix pyrrole derivatives were synthesized.

Article titled "Synthesis of liquid crystals materials derived from oxadiazole, isoxazole and tetrazole heterocycles" by Daniela Rubia dos Santos et al. published in ARKIVOC 2008 (xvii) 157-166 reports The synthesis is described of new liquid crystalline heteroaromatic compounds containing the five-membered isoxazole, tetrazole and 1,2,4-oxadiazole rings.

Article titled "Cesium carbonate catalyzed efficient synthesis of quinazoline-2,4(1H,3H)-diones using carbon dioxide and 2-aminobenzonitriles" by Yogesh P. Patil et al. published in *Green Chemistry Letters and Reviews*, 2008, 1 (2) reports an efficient protocol for the synthesis of quinazoline-2,4(1H,3H)-diones derivatives from 2-aminobenzonitriles with carbon dioxide using catalytic amount of cesium carbonate has been developed.

Article titled "5-Membered N-heterocyclic compounds by dimethyl carbonate chemistry" by Fabio Arico et al. published in *Green Chemistry*, 2012, 14, 58 reports synthesis of N-methoxycarbonyl pyrrolidine starting from 4-amino-1-butanol using DMC as solvent and reagent in the presence of catalytic amount of base. Among the catalysts used, alkali carbonates and in particular $Cs_2CO_3$ resulted the more efficient ones (62% yield).

Article titled "Synthesis of esters derived from 2,3,4-tri-O-benzyl-α-D-methylglucoside" by Tiago A. D. Pinto et al. published in *ARKIVOC* 2012 (vi) 185-193 reports 2,3,4-Tri-O-benzyl-α-D-methylglucoside was prepared and reacted with several acids: benzoic, phenylacetic, 2-(3-bromopropoxy)-benzoic, acetylsalicylic and 4-(toluene-4-sulfonylamino)-benzoic. The products were isolated with low to fair yields and fully characterized by usual analytical techniques.

Article titled "Synthesis, characterization and antioxidant activities of Schiff bases are of cholesterol" by Madasamy Kumar et al. published in *Journal of Saudi Chemical Society*, Available online 4 Apr. 2014 reports synthesis of cholesterylbromo alkyl derivatives and synthesis of cholesteryl aldehyde derivatives.

Article titled "Palladium-Catalysed C—C Coupling: Then and Now" by Chris Barnard published in *Platinum Metals Rev.*, 2008, 52, (1), pp 38-45 reports Heck reactions.

Articled titled "The Synthesis of beta-Nitrostyrenes" by C. B. Gairaud et al. published in *Journal of Organic Chemistry*, 1953, 18, pp 1-3 reports the condensation of nitroalkanes with benzaldehydes to give β-nitrostyrenes has usually been catalyzed by bases such as alcoholic potassium hydroxide or alcoholic methylamine although the reaction was first carried out using an acid catalyst, zinc chloride.

Article titled "Nitrostyrene" by David E. Worrall published in *Organic Syntheses*, Coll. Vol. 1, p. 413 (1941); Vol. 9, p. 66 (1929) reports synthesis of nitrostyrene.

Article titled "Coumarin-derived fluorescent chemosensors" by Hongqi Li et al. published in *Advances in Chemical Sensors* reports coumarin-derived fluorescent chemosensors for $H_2O_2$, $O_2$, hydroxyl radicals or chemical warfare agents in milk samples.

Article titled "Determination of lanthionine by thin-layer chromatography" by Mario Marzona et al. published in *Journal of Chromatography A*, 1968, 32, pp 755-757 reports determination of lanthionine by thin-layer chromatography.

However, development of probes for specific discrimination of biothiols is an unmet need in the art. Probes that are selective to any one of these amino biothiols are very rare in literature. Probes that give specific response with colour change as well as emission change are much needed. Especially those probes which allows real time monitoring without the aid of any instrumental techniques are highly recommended as for as the practical utility is concerned. There are no reports on detection of thiols using simple test strips. Most importantly, those probes which are capable of detecting Cysteine in protein residues are of much significance as such probes are desired for studying complex structures of proteins and their dynamics.

To fulfill this need for the selective detection of thiols, specifically biothiols, with a high degree of selectivity towards cysteine, the inventors have disclosed novel coumarin, and process of synthesis thereof.

OBJECTIVE OF INVENTION

The main objective of the present invention is to provide a novel coumarin derivatives of Formula (L) which are useful for the selective detection of cysteine and process for the preparation thereof.

Another objective of the present invention is to provide a kit for the selective detection of cysteine characterized in that the selectivity of novel coumarin derivatives of Formula (L) to cysteine is 100% and a process for detection using the kit.

Still another objective of the present invention is to provide a process of detection of cysteine in biological fluids and raw milk wherein said process comprising novel coumarin derivatives of Formula (L), characterized in that the selectivity of compound to cysteine is 100%.

Yet another objective of the present invention is to provide a visual as well as fluorescence test for detection of cysteine using novel coumarin derivatives of Formula (L).

Another objective is to develop a suitable protein labeling agent with novel coumarin derivatives.

Still yet another objective of the present invention is to provide a method for the detection of cysteine generated in an enzymatic reaction.

SUMMARY OF THE INVENTION

Accordingly, the present invention provides a novel coumarin derivative of Formula (L) i.e. 7-(dialkylamino)-3-((E)-4-((E)-2-nitrovinyl)styryl)-2H-chromen-2-one which are useful for the selective detection of cysteine.

Formula (L)

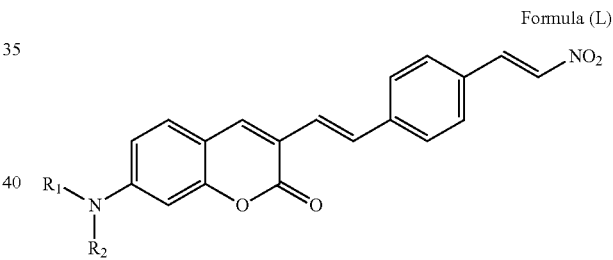

Wherein $R_1$ and $R_2$ are same or different, straight chain alkyl groups, branched chain alkyl groups, preferably selected from methyl and ethyl.

In an embodiment, said coumarin derivatives of formula (L) are selected from 7-(diethylamino)-3-((E)-4-((E)-2-nitrovinyl)styryl)-2H-chromen-2-one and 7-(dimethylamino)-3-((E)-4-((E)-2-nitrovinyl)styryl)-2H-chromen-2-one.

In another embodiment, the present invention provides a process for the preparation of novel coumarin derivatives of Formula (L) comprising the steps of:

a) adding N,N'-Dicyclohexylcarbodiimide (DCC) to a solution of acid in solvent at temperature ranging from 0° C. to 5° C. for the time period ranging from 1-2 hrs followed by addition of substituted salicylaldehyde and 4-Dimethylaminopyridine (DMAP) and stirring the resultant solution at the temperature ranging from 25° C. to 30° C. for the time period ranging from 2-3 hrs;

b) adding caesium carbonate ($CS_2CO_3$) to the filtrate of step (a) followed by stirring the reaction mixture for the time period ranging from 12-14 hrs at the temperature ranging from 25° C. to 30° C. to obtain compound 1;

c) adding aldehyde, coupling agents to a solution of compound 1 of step (b) in solvent followed by heating the reaction mixture for the time period ranging from 12-14 hrs at the temperature ranging from 80° C. to 90° C. under inert atmosphere to afford compound 2.

d) adding base to a solution of compound 2 of step (c) in nitroalkane followed by refluxing for the time period ranging from 3-4 hrs at the temperature ranging from 80° C. to 90° C. to obtain heterocyclic derivatives of Formula (L).

In still another embodiment, the present invention provides a kit for the selective detection of cysteine characterized in that the selectivity of novel coumarin derivatives of Formula (L) to cysteine is 100% and a process for detection using the kit.

In yet another embodiment, the present invention provides a process of detection of cysteine in boilogical fluids and raw milk wherein said process comprising novel coumarin derivatives of Formula (L), characterized in that the selectivity of compound to cysteine is 100%.

In still yet another embodiment, the present invention provides a visual as well as fluorescence test for detection of cysteine using novel coumarin derivatives of Formula (L).

In still yet another embodiment, the present invention provides a method for the detection of cysteine generated in an enzymatic reaction.

In still yet another embodiment the present invention provides a reagent for specific labeling of cysteine residues present in proteins Abbreviations Used GSH: Glutathione
Hcy: Homocysteine
Cys: Cysteine
NAC: N-Acetylcysteine
Probe L: novel coumarin derivatives of Formula (L)
HEPES: (4-(2-hydroxyethyl)-1-piperazineethanesulfonic acid)

DETAILED DESCRIPTION OF THE INVENTION

Figure 1:
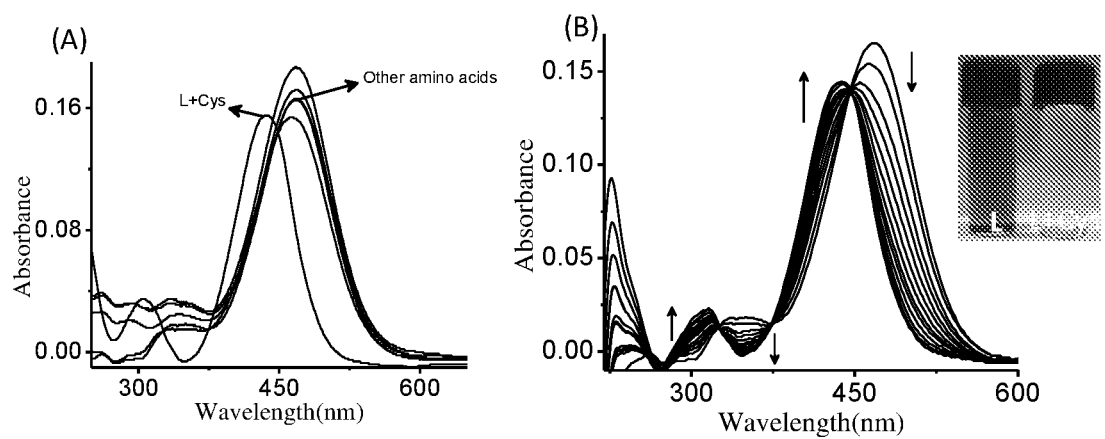
FIG. 1: (A) UV-Vis spectra of L (10 μM) in the absence and presence of various amino acids (AAs); (B) UV-vis changes upon addition of various concentration of Cys (0-100 equiv.).

The invention will now be described in detail in connection with certain preferred and optional embodiments, so that various aspects thereof may be more fully understood and appreciated.

For the purpose of this invention, the expression "probe L" and "coumarin derivatives of Formula (L)" are used interchangeably throughout the specification and both having the same meaning.

The present invention provides a novel coumarin derivative of Formula (L) i.e. 7-(dialkylamino)-3-((E)-4-((E)-2-nitrovinyl)styryl)-2H-chromen-2-one which are useful for the selective detection of cysteine.

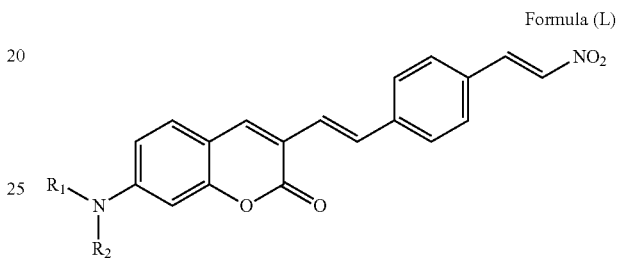

Formula (L)

Wherein $R_1$ and $R_2$ are same or different, straight chain alkyl groups, branched chain alkyl groups, preferably selected from methyl and ethyl.

In an embodiment, said coumarine derivatives of Formula (L) are selected from 7-(diethylamino)-3-((E)-4-((E)-2-nitrovinyl)styryl)-2H-chromen-2-one, and 7-(dimethylamino)-3-((E)-4-((E)-2-nitrovinyl)styryl)-2H-chromen-2-one.

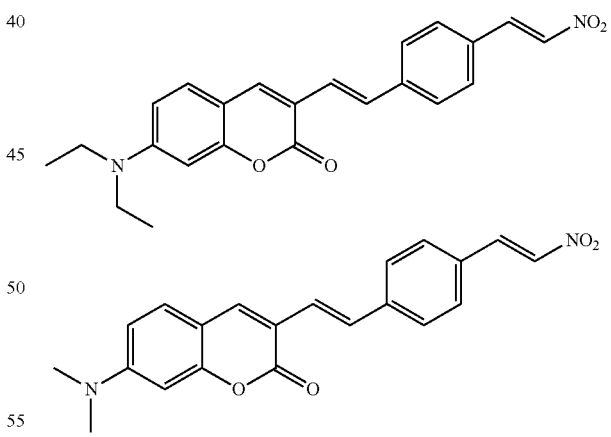

In another embodiment, said coumarin derivatives of Formula (L) is useful for selective sensing of Cysteine (Cys).

In still another embodiment, said coumarin derivatives of Formula (L) can be used to monitor the drug metabolism in living liver cells.

In yet another embodiment, said coumarin derivatives of Formula (L) can be used for monitoring the enzymatic activity of aminoacylase 1, an important enzyme used exclusively in industries for the synthesis of chiral amino acids.

In still yet another embodiment, said coumarin derivatives of Formula (L) is sensitive enough to detect the Cysteine levels in nanomolar range. So, it can be applied to measure the Cysteine levels in bio fluids like blood plasma. Since, any abnormality in Cysteine level is an indicator for many diseases, so this reagent has significance in clinical diagnosis.

In still yet another embodiment, said coumarin derivatives of Formula (L) can detect Cysteine on simple silica coated plate, this is much cheaper and one doesn't need any instrumental techniques for detection.

In still yet another embodiment, said coumarin derivatives of Formula (L) can give visually observable colour change from reddish brown to green upon reaction with Cysteine. This helps in easy detection.

In still yet another embodiment, said coumarin derivatives of Formula (L) can specifically binds to Cysteine present in proteins, this is more advantageous for studying the structure and conformational changes occur in proteins.

In still yet another embodiment, the present invention provides the comparison study of of said coumarin derivatives of Formula (L) with previous prior arts coumarin derivative.

| Coumarin derivatives of formula (L) L | Previous prior art | Previous prior art |
|---|---|---|
| 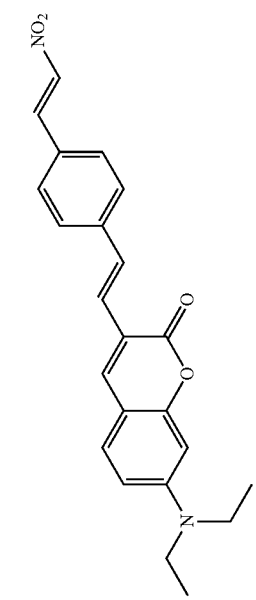 | 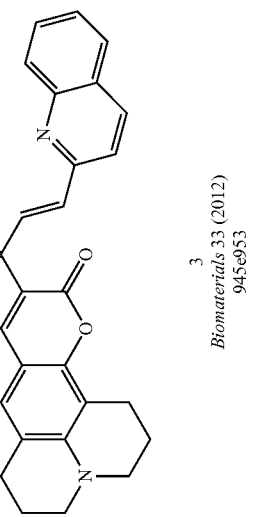 | 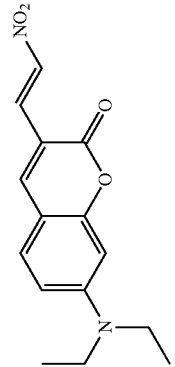 |
| | 3<br>*Biomaterials* 33 (2012) 9456e953 | *Chem. Commun.*, 2011, 47, 11029-11031 |
| 1. This compound is useful for selective sensing of Cysteine (Cys).<br>2. It could be used to monitor the drug metabolism in living liver cells.<br>3. It is useful for monitoring the enzymatic activity of aminoacylase 1, an important enzyme used exclusively in industries for the synthesis of chiral amino acids.<br>4. This reagent is sensitive enough to detect the Cys levels in nanomolar range. So, it could be applied to measure the Cys levels in bio fluids like bllod plasma. Since, any abnormality in Cys level is an indicator for many diseases, so this reagent has significance in clinical diagnosis. | Detect only micromolar range sample. Not sensitive. No colorimetric response. No enzymatic application. No protein labelling application. Useful only in solution. Cannot detect Cys with cheap test strips. | Not specific to Cys Studies were performed in 50% acetonitrile, which is not good. No enzymatic application. No protein labelling Application studies No Test strips. |

-continued

| Coumarin derivatives of formula (L) L | Previous prior art | Previous prior art |
|---|---|---|
| 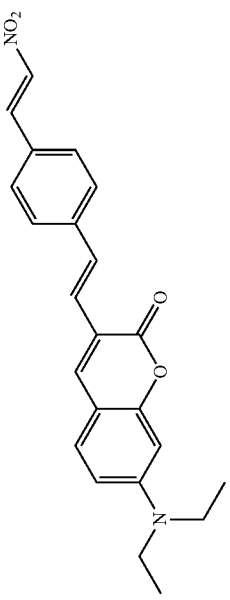 | 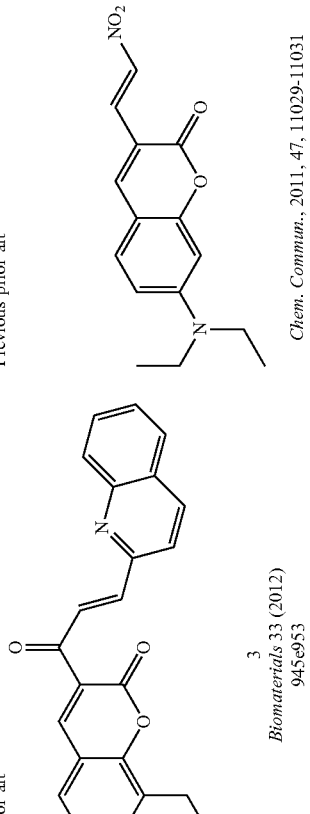  Biomaterials 33 (2012) 945e953 | 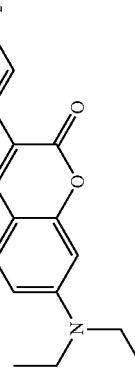  Chem. Commun., 2011, 47, 11029-11031 |

5. This reagent can detect Cys on simple silica coated plate, this is much cheaper and one doesn't need any instrumental techniques for detection.
6. This reagent gives visually observable colour change from reddish brown to green upon reaction with Cys. This helps in easy detection.
7. This reagent specifically binds to Cys present in proteins, this is more advantageous for studying the structure and conformational changes occur in proteins.

In another embodiment, the present invention provides process for the preparation of novel coumarin derivatives of Formula (L) comprising the steps of:
a) adding N,N'-Dicyclohexylcarbodiimide (DCC) to a solution of acid in solvent at temperature ranging from 0° C. to 5° C. for the time period ranging from 1-2 hrs followed by addition of substituted salicylaldehyde and 4-Dimethylaminopyridine (DMAP) and stirring the resultant solution at the temperature ranging from 25° C. to 30° C. for the time period ranging from 2-3 hrs;
b) adding cesium carbonate ($CS_2CO_3$) to the filtrate of step (a) followed by stirring the reaction mixture for the time period ranging from 12-14 hrs at the temperature ranging from 25° C. to 30° C. to obtain compound 1;
c) adding aldehyde, to a solution of compound 1 of step (b) in solvent followed by heating the reaction mixture for the time period of ranging from 12-14 hrs at the temperature ranging from 80° C. to 90° C. under inert atmosphere to obtain compound 2.
d) adding base to a solution of compound 2 of step (c) in nitroalkane followed by refluxing for the time period ranging from 3-4 hrs at the temperature ranging from 80° C. to 90° C. to obtain heterocyclic derivatives of Formula (L).

In a preferred embodiment, said substituted salicylaldehyde is selected from 4-(diehtylamino) salicylaldehyde and 4-(dimethylamino) salicylaldehyde, In another preferred embodiment, said acid is selected from vinyl acetic acid.

In still another preferred embodiment, said solvent of step (a) is dichloromethane.

In yet another preferred embodiment, said coupling agents of step (c) are sodium acetate, triphenyl phosphine and Palladium (II) acetate.

In still yet another preferred embodiment, said solvent of step (c) is dimethylformamide.

In still yet another preferred embodiment, said base of step (d) is ammonium acetate.

In still yet another preferred embodiment, said nitroalkane is selected from nitromethane.

The process for the synthesis for novel coumarin derivatives of Formula (L) is as depicted in Scheme (I);

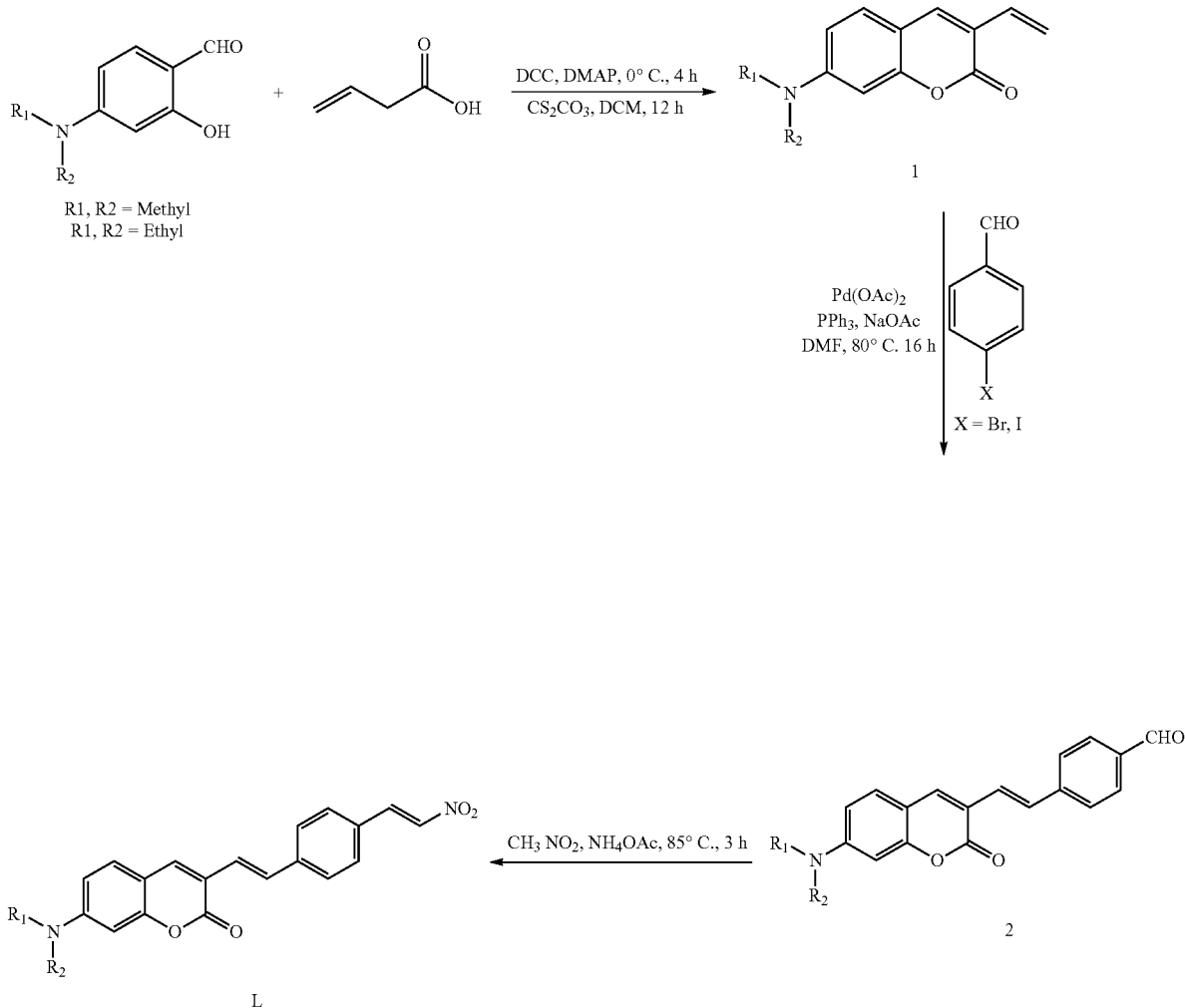

The process for the synthesis for 7-(diethylamino)-3-((E)-4-((E)-2-nitrovinyl)styryl)-2H-chromen-2-one is as depicted in Scheme (II);

Scheme (II)

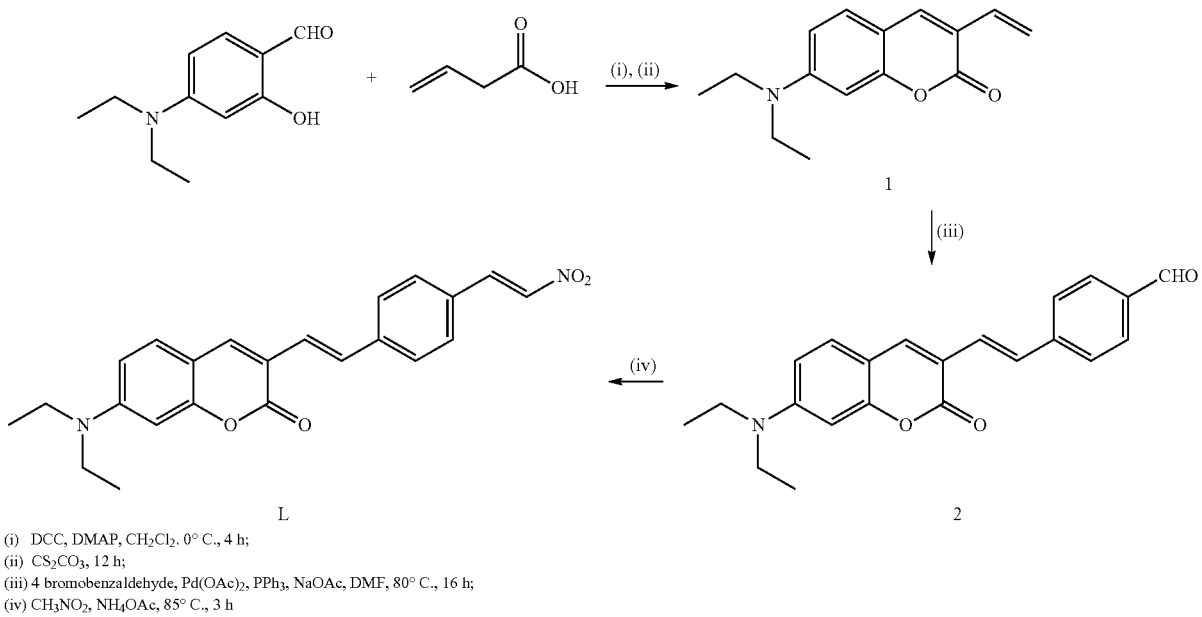

(i) DCC, DMAP, CH$_2$Cl$_2$. 0° C., 4 h;
(ii) CS$_2$CO$_3$, 12 h;
(iii) 4 bromobenzaldehyde, Pd(OAc)$_2$, PPh$_3$, NaOAc, DMF, 80° C., 16 h;
(iv) CH$_3$NO$_2$, NH$_4$OAc, 85° C., 3 h The process comprises DCC coupling of vinyl acetic acid with 4-(diethylamino) salicylaldehyde followed by cyclization in presence of cesium carbonate to result in the formation of vinyl coumarin. Extension of π conjugation achieved by Heck coupling of vinyl coumarin with bromo benzaldehyde, which resulted in an extended aldehyde (compound 2). Incorporation of nitro olefin unit to the parent chromophore was achieved by condensation of aldehyde with nitro methane to get probe L or compound of Formula (L).

In another embodiment, the present invention provides a process of detection of cysteine comprises treating said coumarin derivative of Formula (L) with natural amino acids in HEPES:CH$_3$CN (9:1) at pH 7 characterized in that the selectivity of compound to cysteine is 100%.

In a preferred embodiment, said amino acids are selected from tryptophan (Trp), leucine (Leu), isoleucine (Ile), methionine (Met), threonine (Thr), tyrosine (Tyr), valine (Val), alanine (Ala), serine (Ser), glycine (Gly), cysteine (Cys), glutathione (GSH), homocysteine (Hcy), proline (Pro) and arginine.

Derivatives of coumarin have different substituent at the Nitrogen center (like dimethyl, diethyl etc.). Since the molecule is built for selective sensing purpose, any major change in the heterocyclic coumarin core drastically affects the selectivity and sensitivity.

All the figures provided are showing the sensing behaviour of 7-(diethylamino)-3-((E)-4-((E)-2-nitrovinyl)styryl)-2H-chromen-2-one.

The probe L (10 μM) is treated with natural amino acids (100 equiv. each) in HEPES: ACN (9:1) at pH 7, Only Cys gives an observable change in absorption spectra whereas the other amino acids does not give any significant changes in absorption (FIG. 1A). With the addition of Cys (0-100 equiv.), absorption band at 468 nm gradually decreases and a new band appeared at 438 nm with a visible colour change from red to green (FIG. 1B). A hypsochromic shift (~30 nm) with three well defined isosbestic points are observed at 445 nm, 372 nm and 325 nm. This Cys-induced hypsochromic shift indicates the suppression of ICT process from donor diethylamino unit to acceptor nitroalkene unit.

Figure 8:
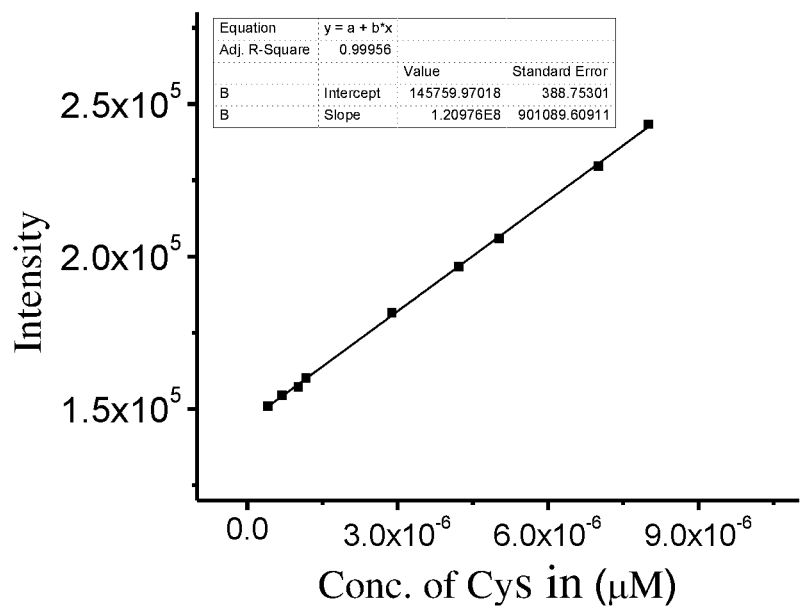
FIG. 8: Fluorescence intensity at 524 nm upon addition of Cys (0-10 μM)

The fluorescence changes of L (10 μM) upon treatment with various amino acids (200 equiv.) in HEPES:CH$_3$CN (9:1) at pH 7 were displayed in FIG. 2A). Only Cys gives an enhancement in the fluorescence compare to all other amino acids. In the absence of Cys, probe L is almost non fluorescent ($\Phi_f$=0.06), upon addition of Cys (0-1000 equiv.), fluorescence intensity is increased remarkably up to 7 fold with an emission band centered at 524 nm ($\lambda_{Ext}$=445 nm) (FIG. 2B). In addition to this, the addition of Cys to solution of L resulted in an observable colour change from non-emissive red to highly emissive green when excited with a hand held 365 nm UV lamp (FIG. 2B, inset). The quantum yield of probe after the addition of Cys increases ($\Phi_f$=0.32) with respect to fluorescein ($\Phi_f$=0.92). The fluorescence turn on response of the probe upon addition of Cys is due to the formation of 1,4 conjugate addition product, which blocks the PET quenching by nitro olefin and also ICT process from diethylamino to nitro olefin unit. The results were in well agreement with our proposed hypothesis. Under identical conditions, other biological thiols such as Hcy and GSH does not give any significant changes in fluorescence (FIG. 2A), which indicates the selectivity of probe towards Cys. The fluorescence intensities of the probe at 524 nm show a good linear relationship with the concentration of Cys between 0 to 1000 μM. The detection limit of Cys is determined as 23.65 nM (23.65×10$^{-9}$) based on S/N=3. (FIG. 8)

Figure 3:
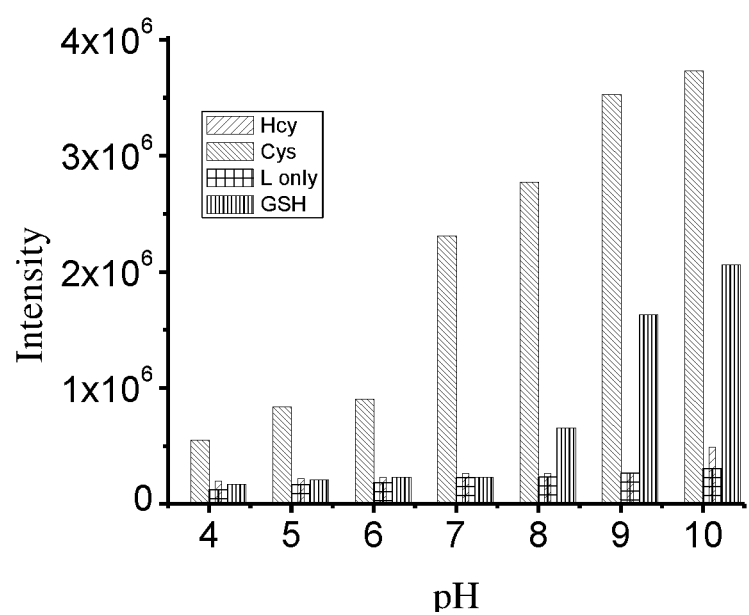
FIG. 3: Change in fluorescence response of L (10 μM) in 10 mM HEPES:CH$_3$CN (9:1 v/v) with Cys, Hcy and GSH upon increase in pH values $\lambda_{Ext}$=445 nm.

Since the pK$_a$ values of Cys, Hcy and GSH are different (8.3, 10.0 and 9.5 respectively), pH dependent study carried out in order to investigate the effect of pH. And the pH studies clearly indicates the selectivity of probe to Cys at pH 7 and the interference from GSH starts with increase in the pH values (FIG. 3). Cys being a low pK$_a$ protein thiol, at neutral pH, the thiolate/thiol ratio is higher for Cys than for Hcy and GSH, which results in greater reactivity of Cys with the probe. This could be the reason for getting selectivity to Cys over Hcy and GSH at pH 7. Also pH 7, being neutral, much suitable for biological studies. Hence, all the studies were carried out at pH 7.

Figure 4:
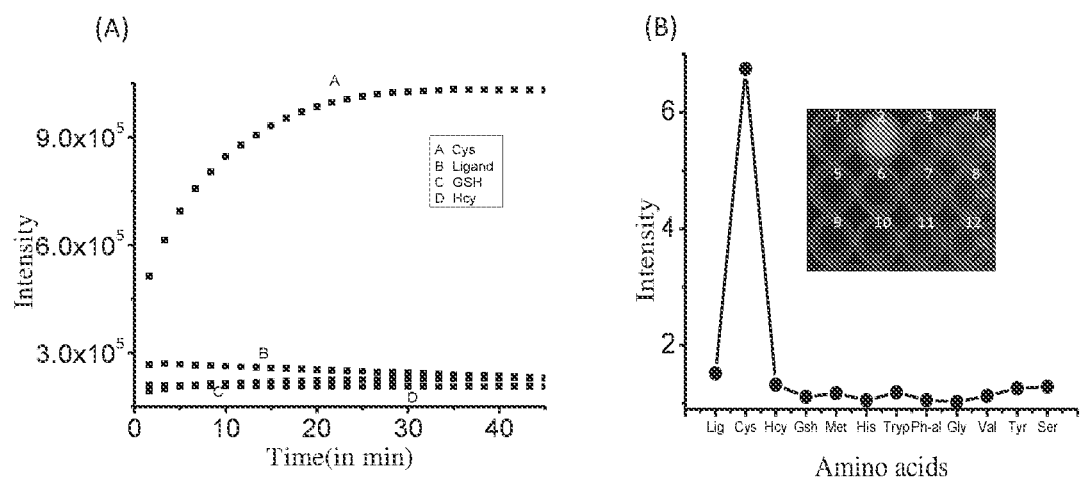
FIG. 4: (A) Time dependent fluorescence response of L (10 μM) with biothiols (Cys, Hcy and GSH) (B) Micro plate fluorescence reading of L with different amino acids.

Time dependent fluorescence response of probe L or compound of Formula (L) is carried out with 200 equiv of Cys. The kinetic study showed that the reaction is completed in 25 minutes. The kinetic study further extended to check the potential interference of Hcy and GSH but no significant changes in the fluorescence observed, which indicates the selectivity of probe towards Cys over Hcy and GSH and it is supported additionally by microplate reading experiment where different amino acid solutions with 10 μM probe in HEPES:ACN (9:1) were taken in a 46 well microplate and the data indicates that only cysteine is giving significant emission changes with respect to other amino acids. (FIG. 4).

In still another embodiment, the present invention provides a kit for the selective detection of cysteine characterized in that the selectivity of novel coumarin derivatives of Formula (L) to cysteine is 100% and a process for detection using the kit.

Figure 7:
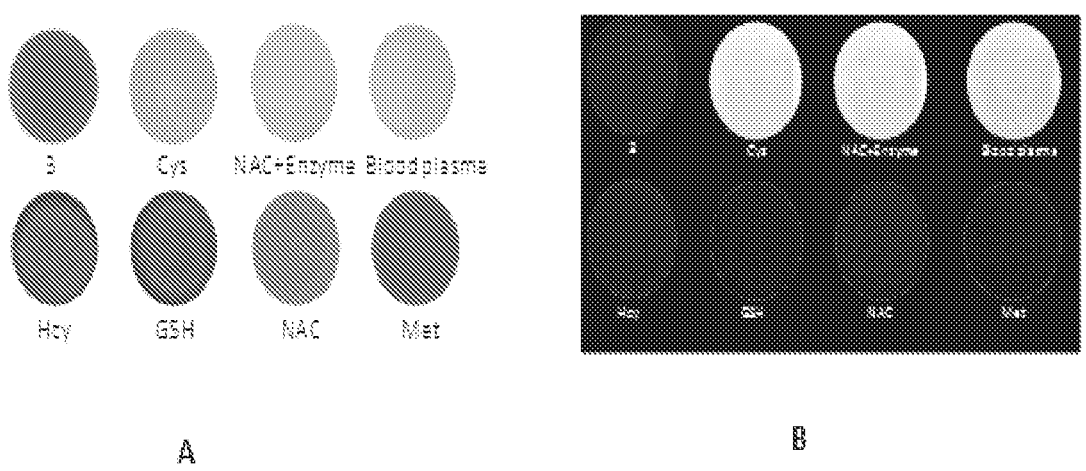
FIG. 7: (A) Visual and (B) Fluorescent color changes of L (5 μM) coated on TLC plates upon addition of different analytes.

In preferred embodiment, the TLC test strips are prepared and with the addition of Cys, the colour of probe coated TLC plates changes from red to yellowish green and becomes highly fluorescent when observed under 365 nm UV lamp (FIG. 7). But Hcy and GSH does not give any observable visible as well as fluorescence changes. The same strategy is further extended to detect Cys in blood plasma and the Cys released in an enzymatic reaction as well. The probe quoted test strips showed visible as well as fluorescent colour changes to Cys as well as Cys present in blood plasma. The same methodology is further extended to detect the enzymatically generated Cys from NAC.

In yet another embodiment, the present invention provides a process for the detection of cysteine present in natural food sources.

In preferred embodiment, the present invention provides a process of detection of cysteine in boilogical fluids and raw milk wherein said process comprising novel coumarin derivatives of Formula (L), characterized in that the selectivity of compound to cysteine is 100%.

In still yet another embodiment, the present invention provides a visual test for detection of cysteine using novel coumarin derivatives of Formula (L).

In preferred embodiment, the present invention provides the nitro olefin based colorimetric as well as fluorescent probe for selective discrimination of Cys over Hcy and GSH. The probe L exhibits high selectivity to Cys, over other amino acids through Michael addition reaction of Cys with probe. The detection limit is found to be 23.65 nM. The probe L which is successfully utilized for the detection of enzymatically generated Cys.

In still yet another embodiment, the present invention provides a method of the detection of cysteine generated in an enzymatic reaction.

Figure 5:
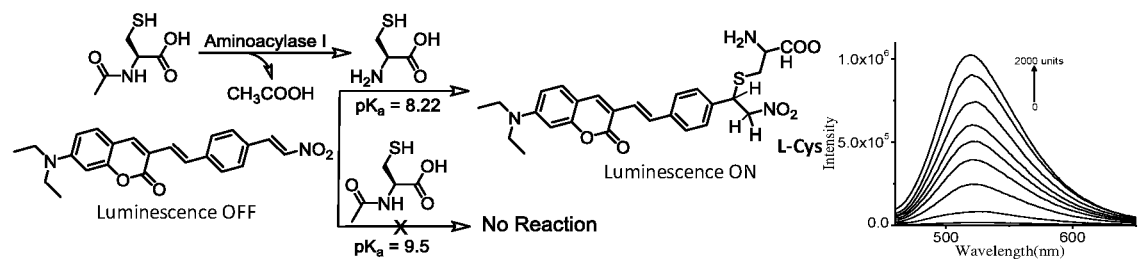
FIG. 5: Fluorescence response of L (10 μM) with NAC (200 equiv.) in presence of amino acylase-1.
Figure 6:
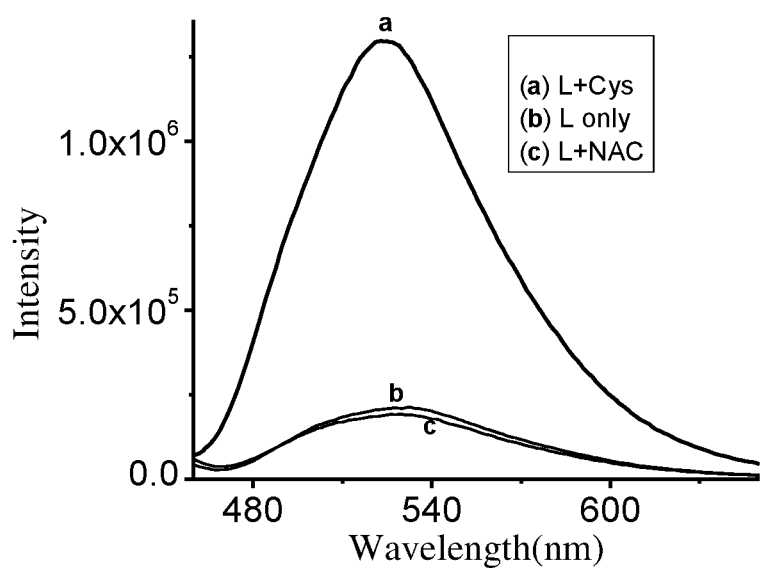
FIG. 6: Fluorescence response of probe (10 μM) with Cys and N-acetyl cysteine.

In another preferred embodiment, the detection of Cys generated in an enzymatic reaction is studied. N-acetyl-cysteine (NAC) is employed as substrate and amino acylase-1 as an enzyme. N-acetyl-cysteine, an acetylated form of Cys, a well known pro-drug used as a cysteine supplement in treatment of glutathione replenishment, acetaminophen over dose, HIV patients etc. NAC supplement releases the Cys inside the cells. Since both Cys as well as NAC has free sulfhydril groups, ideally both should bind with the probe but the higher $pK_a$ value of NAC ($pK_a$=9.5) hinders its reactivity towards the probe at pH 7. Hence, the interference from NAC could be avoided at pH 7 (FIG. 6). Amino acylases are a class of enzymes which specifically hydrolyses the N-acetylated amino acids to release the free amino acids. There are many amino acylases known for de-acetylation of acetylated amino acids, among them Amino acylase-1 is well known for its ability to hydrolyse acetylated cysteine. In the current study, it can be utilized the luminescence ON response for L-Cys formation due to a reaction between L and Cys, released by enzymatic action of aminoacylase-1 on NAC (FIG. 5) In absence of any aminoacylase-1, no change in emission intensity was observed at 520 nm (FIG. 5). After the addition of aminoacylase-1, fluorescent intensity gradually increases, which indicates the efficient hydrolysis of NAC by aminoacylase-1.

Figure 9:
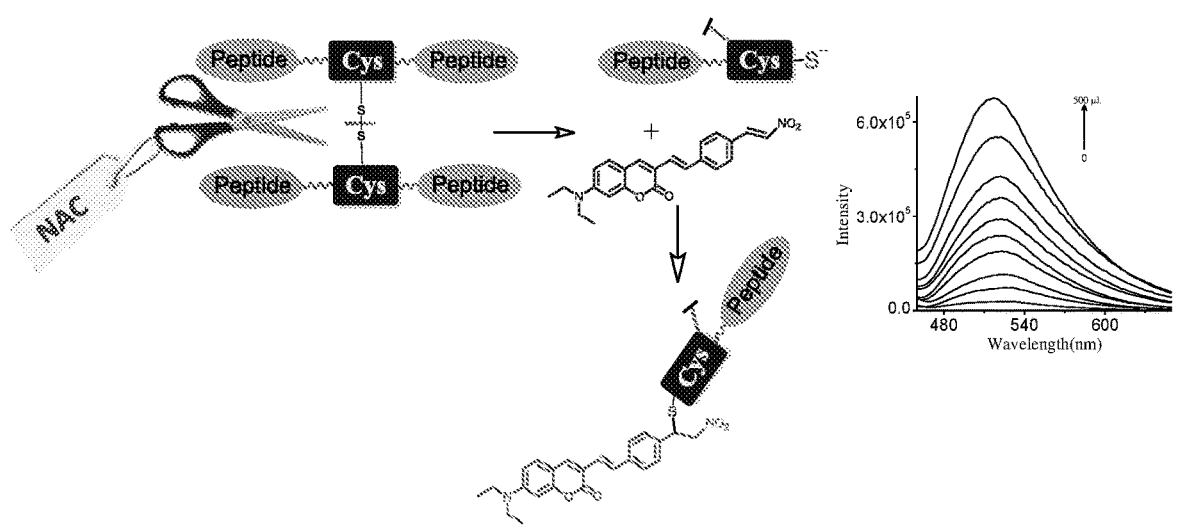
FIG. 9: Fluorescence response of L (10 μM) with Whey protein (500 μl) after hydrolysis with NAC (0-500 μl).

Suitability of this reagent for specific recognition and estimation of Cys-residues present in natural milk proteins was also explored. For this study whey protein was isolated from milk. Initially some fluorescence was observed, which is due to the presence of free Cys. Then NAC tablets are used to reduce the disulfides present in whey. Upon addition of different concentrations of whey and NAC to L, the fluorescence intensity of L gradually increases, indicating the reduction of disulfides by NAC to release Cysteine (FIG. 9). So, this reagent could be used as protein labeling agent to specifically label the Cys present in proteins.

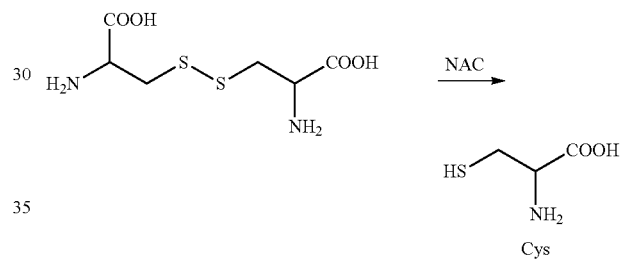

FIG. 1 depicts (A) UV-Vis spectra of L (10 μM) in the absence and presence of various amino acids (AAs); e.g. Tryptophan (Trp), Leucine (Leu), Isoleucine (Ile), Methionine (Met), Threonine (Thr), Tyrosine (Tyr), Valine (Val), Alanine (Ala), Serine (Ser), Glycine (Gly), Cysteine (Cys), Glutathione (GSH), Homocysteine (Hcy), Proline (Pro) and Arginine (Arg); (B) UV-vis changes upon addition of various concentration of Cys (0-100 equiv.). Inset-Visible colour change observed upon addition of Cys. All studies were performed in 10 mM HEPES:$CH_3CN$ (9:1, v/v) at pH 7 at 298 K.

Figure 2:
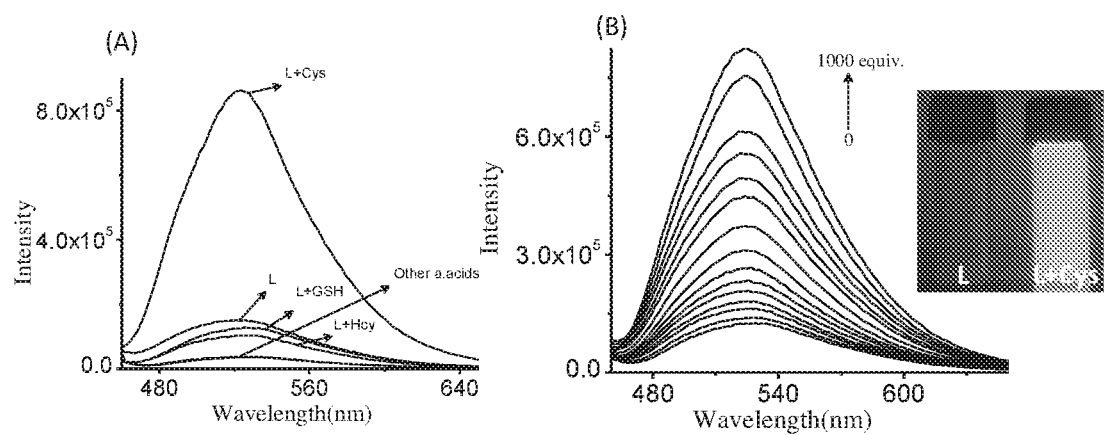
FIG. 2: (A) Luminescence response of L (10 μM) in the absence and presence of various amino acids (AAs); (B) Luminescence changes upon addition of various concentration of Cys (0-1000 equiv.).

FIG. 2 depicts (A) Luminescence response of L (10 μM) in the absence and presence of various amino acids (AAs); (B) Luminescence changes upon addition of various concentration of Cys (0-1000 equiv.). Inset: fluorescence colour change observed under hand held 365 nm UV lamp. All studies were performed in 10 mM HEPES: ACN (9:1) v/v at pH 7 at 298K FIG. 3 depicts change in fluorescence response of L (10 μM) in 10 mM HEPES:$CH_3CN$ (9:1, v/v) with Cys, Hcy and GSH upon increase in pH values $\lambda_{Ext}$=445 nm.

FIG. 4 depicts (A) Time dependent fluorescence response of L (10 μM) with biothiols (Cys, Hcy and GSH) 200 equiv. each in 10 mM HEPES:$CH_3CN$ (9:1, v/v) at pH7, $\lambda_{Ext}$=445 nm; (B) Micro plate fluorescence reading of L with different amino acids. Inset-fluorescent color change observed under UV lamp. (From 1-12. L only, cys, Hcy, GSH, Met, His, Tryp, Ph-al, Gly, Val, Tyr, Ser)

FIG. 5 depicts the mechanism of hydrolysis of NAC by aminoacylase-1 and the corresponding fluorescence response of L (10 µM) with NAC (200 equiv.) in presence of amino acylase-1.

FIG. 6 depicts fluorescence response of probe (10 µM) with Cys and N-acetyl cysteine.

FIG. 7 depicts (A) Visual and (B) Fluorescent color changes of L (5 µM) coated on TLC plates upon addition of different analytes. Fluorescent color changes were observed under hand held 365 nm UV lamp.

FIG. 8 depicts fluorescence intensity at 524 nm upon addition of Cys (0-10 µM).

FIG. 9 depicts the mode of reaction of L with whey protein and fluorescence response of L (10 µM) with Whey protein (500 µl) after hydrolysis with NAC (0-500 µl).

The following examples, which include preferred embodiments, will serve to illustrate the practice of this invention, it being understood that the particulars shown are by way of example and for purpose of illustrative discussion of preferred embodiments of the invention.

EXAMPLES

General Procedure:

Different substituted salicylaldehyde on DCC coupling with vinyl acetic acid in the presence of catalytic amount of DMAP followed by cyclisation in presence of base gives vinyl coumarin. Heck reaction of vinyl coumarin with halobenzaldehyde gives the intermediate aldehyde, which upon condensation with nitromethane in presence of base gives final product.

Same synthetic methods were followed for the synthesis of other derivatives with different substituted salicylaldehydes.

Example 1: Synthesis of [7-(diethylamino)-3-vinyl-2H-chromen-2-one]

Under $N_2$ atmosphere, to a solution of vinyl acetic acid (0.28 mL, 3.23 mmol) in dry $CH_2Cl_2$, DCC (667.45 mg, 3.23 mmol) was added and stirred at 0° C. for 1 hr. To this, 4-(diehtylamino) salicylaldehyde (500 mg, 2.58 mmol) and DMAP (40 mg, 0.32 mmol) were added and it was stirred at room temperature for 3 hrs. Reaction was monitored by TLC. Once the reaction was completed, the solid was filtered and to the filtrate $CS_2CO_3$ (843 mg, 2.58 mmol) was added and it was stirred for 12 hrs to complete the reaction. The mixture was washed with $H_2O$, dried, concentrated under vacuum. The crude product was purified by column chromatography to give vinylcoumarin as greenish yellow solid. Since the compound is labile, it was stored in cold condition. Yield-56%. IR (film) vmax: 1707 (CO), 1597 (C=C), 3017 (—C=C—H) cm$^{-1}$. $^1$H NMR (CDCl$_3$, 400 MHz): δ (ppm) 1.19 (6H, t, CH$_3$), 3.38 (4H, q, CH$_2$), 5.26 (1H, d, J=11.45 Hz, CH), 5.98 (1H, d, J=17.40 Hz), 6.65 (1H, J=17.80 Hz, CH), 7.55 (1H, s), 6.55 (1H, dd, J=8.7 Hz and J=2.75 Hz), 6.45 (1H, d), 7.23 (1H, S). $^{13}$C NMR (CDCl$_3$, 500 MHz): δ (ppm) 12.48, 44.83, 97.09, 109, 115.75, 117.86, 128.87, 131.16, 135.54, 150.50, 155.80, 161.35. HRMS (ESI): m/z calculated for $C_{15}H_{18}NO_2$ [M+H]$^+$ 244.31 found 244.1331.

Example 2: Synthesis of (E)-4-(2-(7-(diethyl-amino)-2-oxo-2H-chromen-3-yl)vinyl)benzaldehyde Vinylcoumarin (75 mg, 0.30 mmol) was taken in dry DMF, to this 4-bromobenzaldehyde (64 mg, 0.36 mMol), sodium acetate (28 mg, 0.33 mmol) and triphenyl phosphine (64.67 mg, 0.24 mmol) was added and it was purged with $N_2$ and was added Pd(OAc)$_2$ (14 mg, 0.06 mmol). It was heated for 16 hrs at 80° C. under inert atmosphere; the completion of the reaction was monitored by TLC. Reaction mass was washed with $H_2O$ and brine solution, dried, concentrated under vacuum. The crude product was purified by column chromatography to give compound 2 as an orange red solid. Yield-80%. IR (film) vmax: 1696 (—CHO), 1612 (C=C), 3021 (—C=C—H) cm$^{-1}$. $^1$H NMR (CDCl$_3$, 400 MHz): δ (ppm) 1.25 (6H, t, CH$_3$), 3.46 (4H, q, CH$_2$), 6.52 (1H, d, J=1.96 Hz), 6.63 (1H, dd, J=8.8 Hz), 7.20 (1H, J=16.14 Hz), 7.28 (1H, t, J=8.80 Hz), 7.55 (1H, d, J=16.38 Hz), 7.65 (2H, d, J=8.07 Hz), 7.73 (1H, s), 7.85 (2H, d, J=8.07 Hz), 9.99 (1H, s, CHO). $^{13}$C NMR (CDCl$_3$, 400 MHz): δ (ppm) 12.49, 44.93, 97.11, 109.30, 116.83, 126.87, 128.58, 129.15, 130.21, 135.16, 139.77, 143.98, 150.90, 155.89, 161.15, 191.63. HRMS (ESI): m/z calculated for $C_{22}H_{21}N_2O_3$ [M+H]$^+$ 348.42 found 348.1591.

Example 3: Synthesis of 7-(diethylamino)-3-((E)-4-((E)-2-nitrovinyl)styryl)-2H-chromen-2-one (L)

Compound 2 (80 mg, 0.23 mmol) was dissolved in nitro methane (8 mL) and was added ammonium acetate (170 mg, 2.30 mmol). It was refluxed at the 85° C. for 3 hrs and reaction was monitored by TLC. After the completion of reaction, reaction mass was concentrated under vacuum and purified by column chromatography to give compound L as red solid. Yield-49%. IR (film) vmax: 1701 (CO), 1506 (N—O), 1615 (C=C), 3024 (—C=C—H) cm$^{-1}$. $^1$H NMR (DMSO-d$_6$, 400 MHz): δ (ppm) 1.14 (6H, t, CH$_3$), 3.45 (4H, q, CH$_2$), 6.57 (1H, s), 6.74 (1H, d, J=8.80 Hz), 7.27 (1H, d, J=16.14 Hz), 7.47 (1H, d, J=8.80 Hz), 7.53 (1H, d, J=16.38 Hz), 7.64 (2H, d, J=8.07 Hz), 7.84 (2H, d, J=8.07 Hz), 8.10 (1H, s), 8.14 (1H, d, J=15.45 Hz), 8.22 (1H, J=13.45 Hz). $^{13}$C NMR (DMSO-d$_6$, 400 MHz): δ (ppm) 12.83, 44.64, 96.74, 108.85, 109.99, 116.08, 126.78, 127.30, 128.40, 129.66, 130.16, 130.96137.85, 139.43, 141.25, 141.78, 151.21, 155.93, 160.59. HRMS (ESI): m/z calculated for $C_{23}H_{22}N_2O_4$ [M+H]$^+$ 391.45 found 391.1651.

Example 4: Synthesis of 7-(dimethylamino)-3-vinyl-2H-chromen-2-one 4-(dimethylamino)salicylaldehyde was used as starting compound and same experimental procedure was followed. Yield 53%. $^1$H NMR (CDCl$_3$, 400 MHz): δ (ppm) 3.08 (6H, s, CH$_3$), 3.38, 7.23 (1H, d, J=11.00 Hz), 6.70 (1H, dd, J=8.70 Hz), 6.61 (1H, J=8.80 Hz), 6.51 (1H, s), 6.07 (1H, d, J=17.61 Hz), 5.32 (1H, d, J=11.25 Hz). $^{13}$C NMR (CDCl$_3$, 100 MHz): δ (ppm) 40.19, 97.66, 109.31, 116.11, 128.63, 131.10, 138.52, 150.50, 155.80, 161.35.

Example 5: Synthesis of (E)-4-(2-(7-(dimethyl-amino)-2-oxo-2H-chromen-3-yl)vinyl)benzaldehyde Vinyl derivative obtained in the above step is coupled with bromobenzaldehyde using the same procedure mentioned previously. Yield 69%. $^1$H NMR (CDCl$_3$, 400 MHz): δ (ppm) 3.06 (6H, s, CH$_3$), 6.62 (1H, d, J=1.93 Hz), 6.68 (1H, dd, J=8.80 Hz), 7.21 (1H, J=16.16 Hz), 7.29 (1H, t, J=8.78 Hz), 7.53 (1H, J=16.33 Hz), 7.68 (2H, d, J=8.17 Hz), 7.70 (1H, s), 7.83 (2H, d, J=8.07 Hz), 9.99 (1H, s, CHO). $^{13}$C NMR (CDCl$_3$, 100 MHz): δ (ppm) 41.13, 97.16, 109.33, 115.83, 124.87, 127.51, 128.15, 130.11, 134.12, 139.71, 143.93, 150.90, 155.81, 161.16, 191.68.

Example 6: Synthesis of 7-(dimethylamino)-3-((E)-4-((E)-2-nitrovinyl)styryl)-2H-chromen-2-one Same procedure was followed as mentioned previously. Yield 43%. $^1$H NMR (DMSO-$d_6$, 400 MHz): δ (ppm) 3.05 (6H, s, CH$_3$), 6.67 (1H, s), 6.80 (1H, d, J=8.80 Hz), 8.22 (1H, d, J=13.69 Hz), 8.13 (2H, d, J=8.80 Hz), 7.85 (2H, d, J=8.80 Hz), 7.66 (2H, d, J=8.07 Hz), 7.54 (2H, d, J=11.25 Hz), 7.49 (1H, d, J=9.05 Hz), 7.28 (1H, d, J=16.38 Hz), 8.22 (1H, J=13.45 Hz). $^{13}$C NMR (DMSO-$d_6$, 400 MHz): δ (ppm) 41.14, 95.71, 108.80, 108.91, 116.83, 126.70, 127.10, 128.10, 129.16, 130.66, 130.13, 139.43, 141.15, 141.68, 151.12, 155.33, 160.69.

Example 7: General Experimental Methods for UV-Vis and Fluorescence Studies $5 \times 10^{-3}$M stock solution of 7-(diethylamino)-3-((E)-4-((E)-2-nitrovinyl)styryl)-2H-chromen-2-one was prepared in CH$_3$CN and the same solution was used for all the studies after appropriate dilution. Unless and otherwise mentioned, 10 mM and pH 7 solution of aq. HEPES buffer was used for all spectroscopic studies. All amino acid solutions of $1.0 \times 10^{-1}$M were prepared in HEPES buffer (pH 7). For spectroscopic measurements, stock solution of the probe was further diluted by using HEPES:CH$_3$CN (9:1) mixture and the effective final concentration was made as 10 μM. All luminescence measurements were done using $\lambda_{ext}$=445 nm with an emission slit width of 2 nm. The fluorescence quantum yield was determined according to literature method using fluorescein (in 0.1M NaOH) as reference ($\Phi_f$=0.92).

Example 8: General Procedure for Enzymatic Study

Cipla made effervescent tablets of N-Acetyl-Cysteine were purchased from commercially available sources. Based on the quantity of NAC present in the tablet, $1.0 \times 10^{-1}$M tablet solution was prepared in 10 mM aq.

HEPES buffer solution (pH7). Enzyme solution was prepared according to the requirement by dissolving 1 mg/ml in 10 mM aq.HEPES buffer solution (pH7). A fixed concentration of NAC (200 equiv.) was added to the 10 μM probe in HEPES:CH$_3$CN (9:1, v/v). Since 1 mg of solid enzyme contains 3301 units of protein and 1 unit can hydrolyse 1 μM of substrate, accordingly enzyme concentration was varied with respect to the substrate concentration.

10 μM of 7-(diethylamino)-3-((E)-4-((E)-2-nitrovinyl) styryl)-2H-chromen-2-one is treated with 200 equiv. of NAC and different concentration of enzyme (0-2000 units) was added and the resulting solution was incubated at 37° C. for the time period ranging from 45 to 50 mins. Initially there is no fluorescence because NAC cannot bind to probe and fluorescence is turned on gradually with time, which indicates the hydrolysis of NAC by Amino acylase-1 to release of Cys. Fluorescence intensity increases with the increase in concentration of enzyme (0 to 2000 units) as more and more amounts of Cys was released from NAC by the enzymatic activity (FIG. 6). Initially, the same experiment in room temperature but reaction was slow, and took more than 90 min. Incubation at the temperature 37° C. aided in faster reaction, which indicates that enzyme activity was much higher at body temperatures.

Example 9: Preparation of TLC Test Strips

TLC test strips were prepared by coating 5 μM of 7-(diethylamino)-3-((E)-4-((E)-2-nitrovinyl)styryl)-2H-chromen-2-one solution in acetonitrile on silica TLC plates. 5 μl of Cys ($1.0 \times 10^{-1}$M) in 10 mM aq.HEPES buffer (pH7) was added on it, dried and the visual as well as fluorescence colour changes were observed after 5 min. The same was repeated for Hcy and GSH as well. To detect Cys in blood plasma, 20 μl of blood plasma was diluted (10 μl plasma+10 μl buffer) was added on probe quoted TLC plate. Same methodology was repeated for enzymatic reaction on TLC plate by using 10 μl of NAC and amino acylase-1 enzyme.

Example 10: General Procedure for Detecting Cysteine from Raw Milk

Raw milk was subjected to fermentation and the liquid whey which was settled above after fermentation process was separated by filtration. A varying amount of whey ranging from 500 μl was added to Probe L (7-(diethylamino)-3-((E)-4-((E)-2-nitrovinyl)styryl)-2H-chromen-2-one) (10 μM) in HEPES:ACN at pH 7. Varying concentrations of N-Acetyl Cysteine (0-500 μl) was added to each of the above solution in order to hydrolyse the bound Cysteine present in whey protein (NAC solution was prepared by dissolving NAC tablets in buffer as mentioned in the enzymatic study). Luminescence changes were recorded after 45-50 minutes of incubation at room temperature. The remaining derivatives of probe L may give similar kind of response.

ADVANTAGES OF INVENTION a) Simple process of detection
b) Selective determination of cysteine
c) Economical advantage of material and process
d) This method is of much practical significance in real time monitoring as it could be done without the aid of any instruments.
e) The present invention provides new pathways for designing the highly selective and sensitive fluorescent probes for Cysteine.
f) Reagent could be used for detection of Cysteine present in milk whey.
g) Reagent can be used for monitoring enzymatic activity.
h) Reagent could be used for labeling the cysteine residues present in proteins, which in turn helps in studying the protein structure and dynamics

We claim:
1. A Coumarin derivative of Formula (L)

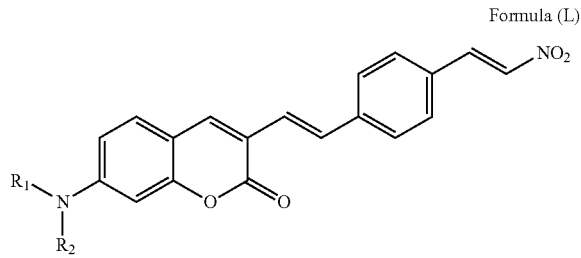

Formula (L)

Wherein $R_1$ and $R_2$ are same or different, straight chain alkyl groups, branched chain alkyl groups.

2. The compound as claimed in claim 1, wherein said compound is selected from 7-(diethylamino)-3-((E)-4-((E)-2-nitrovinyl)styryl)-2H-chromen-2-one and 7-(dimethylamino)-3-((E)-4-((E)-2-nitrovinyl)styryl)-2H-chromen-2-one.

3. A process for the preparation of coumarin derivatives of Formula (L) as in claim 1 comprising the steps of:
   a) adding N,N'-Dicyclohexylcarbodiimide (DCC) to a solution of vinyl acetic acid in dicholoromethane at temperature ranging from 0° C. to 5° C. for the time period ranging from 1-4 hrs followed by addition of substituted salicylaldehyde and 4-Dimethylaminopyridine (DMAP) and stirring the resultant solution at the temperature ranging from 25° C. to 30° C. for the time period ranging from 2-3 hrs;
   b) adding caesium carbonate ($CS_2CO_3$) to the filtrate of step (a) followed by stirring the reaction mixture for the time period ranging from 12-14 hrs at the temperature ranging from 25° C. to 30° C. to obtain compound 1;
   c) adding aldehyde, coupling agents to a solution of compound 1 of step (b) in dimethylformamide followed by heating the reaction mixture for the time period ranging from 12-14 hrs at the temperature ranging from 80° C. to 90° C. under inert atmosphere to obtain compound 2;
   d) adding ammonium acetate to a solution of compound 2 of step (c) in nitromethane followed by refluxing for the time period ranging from 3-4 hrs at the temperature ranging from 80° C. to 90° C. to obtain heterocyclic derivatives of Formula (L).

4. The process as claimed in claim 3, wherein said substituted salicylaldehyde is selected from 4-(diehtylamino) salicylaldehyde and 4-(dimethylamino) salicylaldehyde.

5. The process as claimed in claim 3, wherein said coupling agents of step (c) are sodium acetate, triphenyl phosphine and Palladium (II) acetate.

6. A process of detection of cysteine comprising treating compound formula (L) as claimed in claim 1 with natural amino acids in HEPES: ACN (9:1) at pH 7 characterized in that the selectivity of compound (L) to cysteine is 100%, wherein said amino acids is selected from tryptophan (Trp), leucine (Leu), isoleucine (Ile), methionine (Met), threonine (Thr), tyrosine (Tyr), valine (Val), alanine (Ala), serine (Ser), glycine (Gly), cysteine (Cys), glutathione (GSH), homocysteine (Hcy), proline (Pro) and arginine.

7. A process of enzymatic estimation of cysteine using compound (L) as claimed in claim 1 comprising the steps of:
   a) adding N-Acetyl-Cysteine to the probe L in HEPES: $CH_3CN$ (9:1) followed by adding different concentration of Amino acylase-1 solution;
   b) incubating resulting solution at 37° C. for 45 min.

8. The process as claimed in claim 7, wherein said process is taking place at pH 7.

9. A visual test for detection of cysteine using compound (L) as claimed in claim 1 comprising the steps of:
   a) preparing thin layer chromatography test strips by coating probe L solution in acetonitrile on silica TLC plates;
   b) adding Cystein in aq.HEPES buffer (pH7) on it;
   c) drying for 5-10 mins and observing visual as well as fluorescence colour changes;
      said test is used in enzymatic reaction on TLC plate by using of NAC and amino acylase-1 enzyme.

10. A process of detection of cysteine in biological fluids and raw milk (whey) using compound (L) as claimed in claim 1 comprising the steps of:
   a) adding different amount of whey to probe L in HEPES: ACN at pH 7;
   b) adding different concentrations of N-Acetyl Cysteine to each of the above solution of step (a); and
   c) incubating at 37° C. for 45 minutes and recording luminescence changes.

* * * * *